(12) United States Patent
Randolph

(10) Patent No.: US 6,632,090 B1
(45) Date of Patent: *Oct. 14, 2003

(54) METHOD AND SYSTEM FOR DISPENSING PROPHYLAXIS MEDIUM

(76) Inventor: Bradley A. Randolph, 724 1/2 Ave. G, Fort Madison, IA (US) 52627

( * ) Notice: Subject to any disclaimer, the term of this patent is extended or adjusted under 35 U.S.C. 154(b) by 0 days.

This patent is subject to a terminal disclaimer.

(21) Appl. No.: 09/683,841

(22) Filed: Feb. 21, 2002

Related U.S. Application Data

(63) Continuation-in-part of application No. 09/681,565, filed on Apr. 30, 2001, now Pat. No. 6,382,971.

(51) Int. Cl.$^7$ ................................................ A61C 1/00
(52) U.S. Cl. ......................................... 433/82; 433/125
(58) Field of Search ............................... 433/82, 83, 84, 433/85, 166, 125

(56) References Cited

U.S. PATENT DOCUMENTS 2,300,828 A * 11/1942 Goldenberg ................ 433/166
5,911,577 A    6/1999 Henrikson

* cited by examiner

Primary Examiner—Cary E. O'Connor
(74) Attorney, Agent, or Firm—Simmons, Perrine, Albright & Ellwood, PLC

(57) ABSTRACT

A system and method for dispensing prophylaxis paste during dental cleaning procedures which includes a flow control valve, which is actuated by pressure between the prophy cup and the tooth, and also includes a source of prophylaxis paste delivered under pressure.

26 Claims, 4 Drawing Sheets

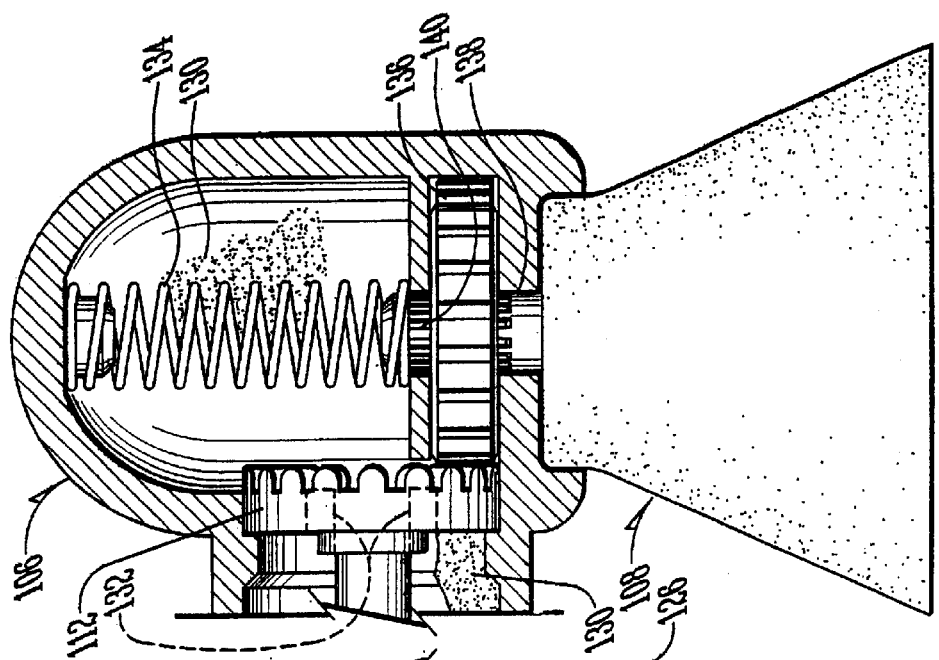
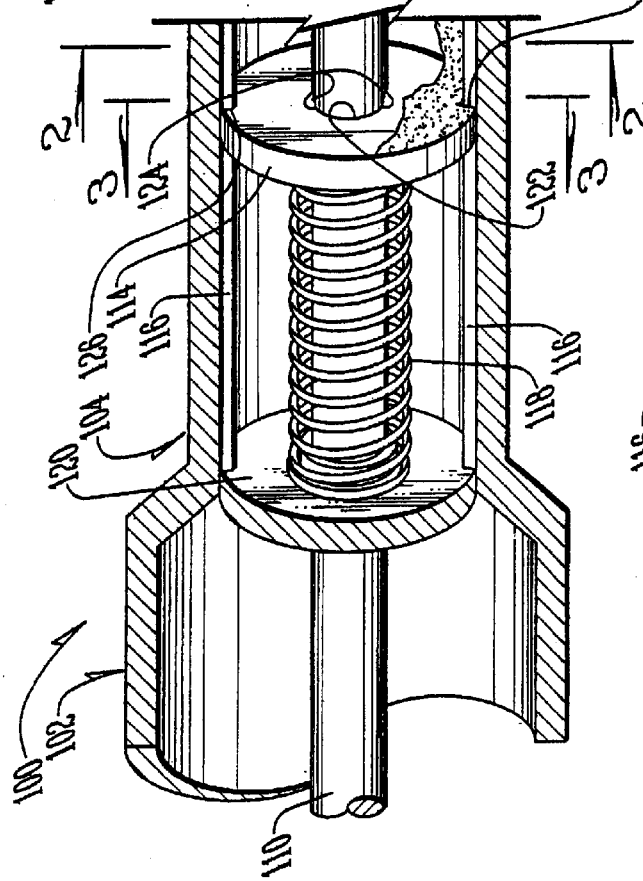
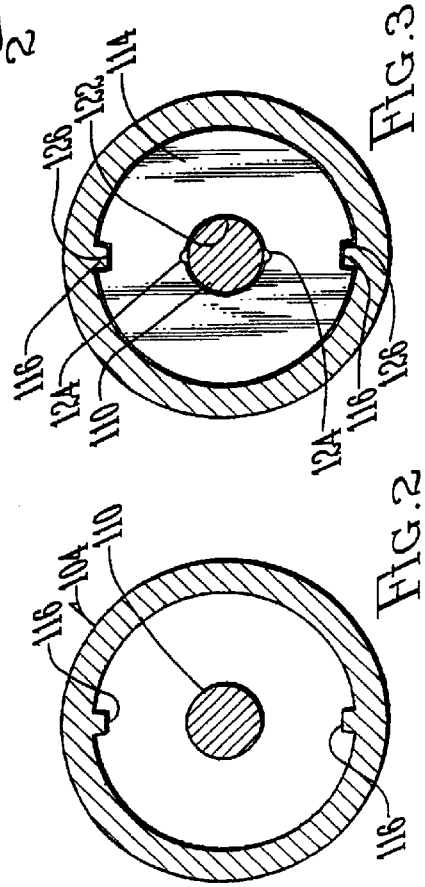
Fig. 1
Fig. 2
Fig. 3

METHOD AND SYSTEM FOR DISPENSING PROPHYLAXIS MEDIUM

CROSS REFERENCE TO RELATED APPLICATION

The present invention is a continuation-in-part application of an earlier invention having the same title, filed by the same inventor on Apr. 30, 2001, and having Ser. No. 09/681,565, now U.S. Pat. No. 6,382,971, which application is incorporated herein in its entirety by this reference.

BACKGROUND OF THE INVENTION

The health industry, as it relates to treating patients, has an ever-increasing concern and duty to minimize the risk of the spread of diseases. Treatments that involve either a person's bodily fluids, such as saliva or those that come in contact with potential blood-borne pathogens, create an ever-constant threat of cross-contamination. The use of a disposable prophy angle by the dental profession to aid in proper tooth care and oral hygiene has helped reduce such risks.

While these disposable prophy angles have been used extensively in the past, they do have some drawbacks. First of all, the dentist is typically required to utilize a separate container of prophylaxis paste and to refill the prophy cup several times during a typical cleaning procedure. This refilling of the prophy cup requires the dentist to remove the instrument from the patient's mouth and refill the cup. This repeated removal of the instrument increases the risk of a transfer of a patient's saliva, food debris, or plaque and potential associated blood-borne pathogens.

Attempts have been made in the past to provide a paste delivery system which is integral to the prophy angle. Examples are described in U.S. Pat. No. 5,871,353 issued to Pierce et al. for PROPHY ANGLES WITH DENTIFRICE DISPENSING SYSTEMS, issued on Feb. 16, 1999; U.S. Pat. No. 5,692,901 issued to Roth et al. for a DISPOSABLE ADJUSTABLE FLOW PROPHY ANGLE, issued on Dec. 2, 1997; and U.S. Pat. No. 3,977,083, issued to Leslie et al. for a DENTAL INSTRUMENT issued on Aug. 31, 1976, all of which patents are incorporated herein in their entirety by these references. These prophy angles used various approaches, including an auger to move paste from a reservoir to the cup. Some of these designs also included flow regulation by merely tying the flow rate to the rotation rate of the cup and the auger, and others used an externally adjusted knob. These devices each have shortcomings.

Merely tying the dentifrice flow rate to cup rotation rate is most often undesirable because the need for paste is not always proportional to the rotation rate or consistent with the relative speed at which each practitioner utilizes the prophy angle. For example, some practitioners work with faster rotation rates than others. In such situations, the paste may run out before the prophylaxis is completed. This becomes costly and inefficient.

The manually adjusted flow control knob of the Roth design requires the dentist to remove the instrument from the patient's mouth and then manually adjust the knob. Then the device is reinserted into the patient's mouth. This removal and reinsertion is time consuming, and it, too, increases the risk of cross-contamination.

Consequently, there exists a need for improved methods and systems for dispensing prophylaxis paste in a sanitary and efficient manner.

SUMMARY OF THE INVENTION

It is an object of the present invention to provide a system and method for dispensing prophylaxis medium in a sanitary and efficient manner.

It is a feature of the present invention to utilize a pressure sensitive flow valve coupled to a prophy cup.

It is another feature of the present invention to include a pressurized medium provisioning assembly.

It is an advantage of the present invention to achieve improved efficiency in dispensing medium during dental procedures.

The present invention is an apparatus and method for dispensing prophylaxis medium, which is designed to satisfy the aforementioned needs, provide the previously stated objects, include the above-listed features, and achieve the already articulated advantages. The present invention is carried out in a "contamination-less" and "wasted effort-less" manner in a sense that the potential for cross-contamination and the extra effort associated with removing the prophy angle from the patient's mouth and then reinserting it have been greatly reduced.

Accordingly, the present invention is a system and method including a prophy angle with a pressure sensitive flow valve, which is actuated by engaging the tooth with the prophy cup and increasing the pressure therebetween and thereby increasing the flow rate of medium into the prophy cup.

BRIEF DESCRIPTION OF DRAWINGS

The invention may be more fully understood by reading the following description of the preferred embodiments of the invention, in conjunction with the appended drawings wherein:

FIG. 1 is a cut-away side view of a system of the present invention.

FIG. 2 is a cross-section view taken on line 2—2 of FIG. 1.

FIG. 3 is a cross-section view of the plunger disk taken on line 3—3 of FIG. 1.

DETAILED DESCRIPTION

Figure 5:
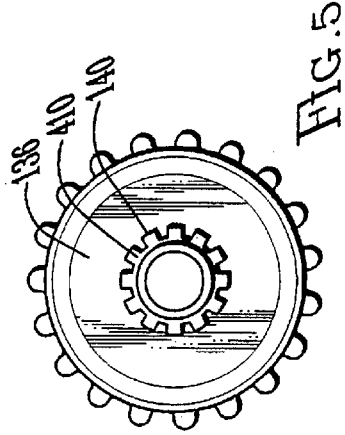
FIG. 5 is a top view of the horizontal cup drive gear with the top side of cup drive tube shown centrally disposed therein.

Now referring to the drawings wherein like numerals refer to like matter throughout, and more specifically referring to FIG. 1, there is shown a system of the present invention generally designated 100, including a hollow prophy angle main body 102, with a hollow prophy angle paste pressurization section 104 adjacent thereto. Coupled to prophy angle paste pressurization section 104 is prophy angle head section 106, which has a prophy cup 108 coupled thereto. Throughout this description of the present invention, numerous references are made to paste and prophylaxis paste, etc. It should be understood that when these terms are used to describe the present invention, they are intended to be construed broadly to cover any prophylaxis medium or dentifrice, such as paste, gel or the like. Drive shaft 110 is for coupling with a rotary power source (not shown, but well known in the art). The rotary power source need not be coupled directly to the prophy angle. The prophy angle may be coupled through a separate nose cone to certain rotary power sources. Alternately, the prophy angle can be modified to eliminate the need for a nose cone and thereby couple directly to such rotary power sources. Drive shaft 110 has a drive shaft terminal vertical gear 112 disposed at the opposite end from an end which couples with the power source. Drive shaft terminal vertical gear 112 is preferably a toothed gear. Disposed around drive shaft terminal vertical gear 112, in prophy angle paste pressurization section 104, is pressurizing plunger disk 114, which is adapted to slide along disk alignment ridges 116 with the aid of paste pressurizing spring 118. Disposed centrally in pressurizing plunger disk 114 is drive shaft orifice 122, which receives the drive shaft 110 therein. Spring stop 120 is present to provide a stop for paste pressurizing spring 118. When the prophy angle 100 is initially deployed, it may be desirable to not have the prophylaxis paste 130 being under pressure. This could be accomplished by having pressurizing plunger disk 114 being affixed to drive shaft 110, through a centrally disposed drive shaft orifice 122, at a predetermined position along drive shaft 110. Another advantage to coupling the plunger disk 114 to the drive shaft 100 is to facilitate the initial loading of dentifrice. Pressurizing plunger disk 114 could be affixed, using drive shaft to disk initial couplings 124, which could be drops of glue, or other coupling mechanisms which are sufficiently strong to resist movement of the pressurizing plunger disk 114 along the drive shaft 110, but not so strong as to not be broken when drive shaft 110 is initially caused to rotate. In one embodiment, drive shaft 110 and pressurizing plunger disk 114 may be made from a single piece of plastic material with drive shaft to disk initial couplings 124 thereon. Pressurizing plunger disk 114 may have ridge-receiving grooves 126 therein for cooperating with disk alignment ridges 116 to resist uneven movement of the pressurizing plunger disk 114 along the drive shaft 10 during use. The paste side of pressurizing plunger disk 114 may be rubber coated to help create a seal for one way dispensing of paste and helping to prevent backflow or leakage into pressurized spring area. Other arrangements of the paste pressurizing spring 118, pressurizing plunger disk 114 and entirely different types of devices used to provide matter under pressure are envisioned and intended to be included within the scope of the present invention.

Prophy angle paste pressurization section 104 and prophy angle head section 106 are shown having prophylaxis paste 130 disposed therein. Prophylaxis paste 130 is depicted with dots. These dots are not intended to suggest that particles are suspended in the prophylaxis paste 130, but merely to distinguish it from the other components also shown in the figures. Prophylaxis paste 130 is under pressure within prophy angle paste pressurization section 104 and prophy angle head section 106 by the pressurizing plunger disk 114. Prophylaxis paste 130 is allowed to pass between prophy angle paste pressurization section 104 and prophy angle head section 106 by prophylaxis paste passageways 132 through drive shaft terminal vertical gear 112. Prophylaxis paste passageways 132 may be vents or ports in the head of drive shaft terminal vertical gear 112. Other ways of allowing passage of prophylaxis paste 130 could be employed as well, such as having gear 112 more resemble a spoked wheel/hub with a ring gear periphery.

Prophy angle head section 106 has therein a horizontal cup drive gear 136, which couples with drive shaft terminal vertical gear 112 to transmit power from the power source via drive shaft 110 to the prophy cup 108. Drive shaft terminal vertical gear 112 and horizontal cup drive gear 136 are similar to gears which are well known in the art, except that drive shaft terminal vertical gear 112 has prophylaxis paste passageways 132 therein and horizontal cup drive gear 136 has a central hole therein for receiving cup drive tube 138. Cup drive tube 138 and horizontal cup drive gear 136 are adapted to permit cup drive tube 138 to slide along its longitudinal axis through the central hole in horizontal cup drive gear 136. Horizontal cup drive gear 136 and cup drive tube 138 are also adapted to permit transmission of rotary motion of horizontal cup drive gear 136 into rotary motion of cup drive tube 138. This transmission of motion may be accomplished in many ways, with one example being the use of cup drive tube external gear engaging ridges 140 disposed on cup drive tube 138 which interleave with and cooperate with ridges in the central hole of horizontal cup drive gear 136. Cup drive tube 138 is capable of translational motion through horizontal cup drive gear 136; however, pressure sensitive valve spring 134 is used to bias cup drive tube 138 to a downward position. Other arrangements of the spring and entirely different types of pressure sensitive valves are envisioned and intended to be included within the scope of the present invention.

The prophy angle 100 of the present invention is preferably disposable and made of plastic, rubber or silicon-based material, such as is well known in the art of disposable prophy angles. In a preferred embodiment, paste pressurizing spring 118 and pressure sensitive valve spring 134 may be made of material other than plastic, such as stainless steel or other metals suitable for spring construction and suitable for use in a sanitary application. In another preferred embodiment of the present invention, prophy angle paste pressurization section 104 and prophy angle head section 106 are preferably either transparent or translucent and prophylaxis paste 130 has a dark or contrasting color, so that the amount of paste remaining in the prophy angle 100 can be readily determined by a visual inspection by the dentist.

Now referring to FIG. 2, there is shown a cross-sectional view of the prophy angle paste pressurization section 104 taken along lines 2—2 of FIG. 1. Disk alignment ridges 116 are shown disposed at the top and bottom sections of prophy angle paste pressurization section 104, but other arrangements and numbers of ridges could be used as well.

Now referring to FIG. 3, there is shown a cross-sectional view of the pressurizing plunger disk 114 taken on lines 3—3 of FIG. 1. Pressurizing plunger disk 114 is shown having ridge receiving grooves 126 therein for cooperation with disk alignment ridges 116 (FIGS. 1 and 2). Also shown in pressurizing plunger disk 114 is drive shaft orifice 122, which is adapted to receive drive shaft 110 therethrough, but preferably not permit excess amounts of prophylaxis paste 130 to pass therethrough when pressurizing plunger disk 114 progresses along drive shaft 110 during the paste dispensing process. O-rings or other well-known structures could be employed as well.

Figure 4:
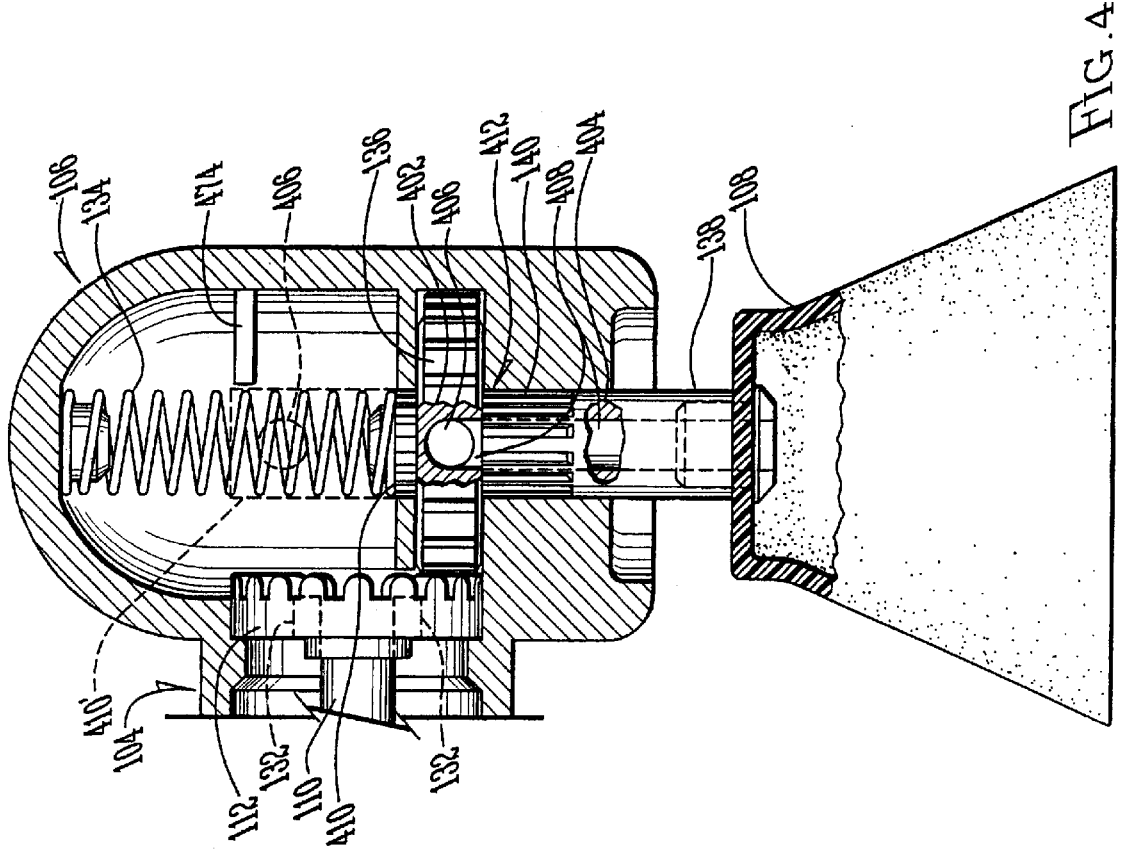
FIG. 4 is an enlarged cut-away side view of the gear and pressure sensitive valve portion of FIG. 1, where dotted lines are used to represent a pressure sensitive valve configuration when pressure is applied to the prophy cup and the paste entry hole is exposed. Two additional internal cut-away portions are used to show the paste entry hole when no pressure is applied and to show the paste delivery channel.

Now referring to FIG. 4, there is shown an enlarged cut-away view of portions of prophy angle paste pressurization section 104 and the prophy angle head section 106 section of the prophy angle 100 of FIG. 1. To reduce the complexity of the drawing, the prophylaxis paste 130 is not shown in FIG. 4. FIG. 4 does include a first cutaway region 402, which is shown centrally disposed over horizontal cup drive gear 136. First cut-away region 402 reveals an upper section of cup drive tube 138, which is disposed in a central hole in horizontal cup drive gear 136. This upper section of cup drive tube 138 is concealed by horizontal cup drive gear 136 in FIG. 1. First cut-away region 402 reveals a paste entry hole 406 disposed in cup drive tube 138. There is also shown a paste delivery channel 408, which extends through cup drive tube 138 from prophy cup 108 to paste entry hole 406. Second cut-away region 404 is shown in a central section of cup drive tube 138, where a portion of cup drive tube 138 has been removed to reveal the paste delivery channel 408 therein. In this enlarged figure, top side 410 of cup drive tube 138 is shown. Top side 410 has a diameter which is larger than the central hole through horizontal cup drive gear 136 or includes some other feature to prevent pressure sensitive valve spring 134 from moving cup drive tube 138 too far into horizontal cup drive gear 136. The combination of pressure sensitive valve spring 134, horizontal cup drive gear 136, cup drive tube 138, paste entry hole 406 and paste delivery channel 408 could be described as a pressure sensitive valve 412. It should be understood that the paste entry hole 406 need not be circular; it may be elliptical, square, or any shape. Hole 406 may be any type of orifice or any interstice between members extending above and below the hole 406.

Cup drive tube 138 may have multiple paste entry holes 406 therein, depending upon desired flow rates. Also, paste entry hole 406 may be configured to extend slightly above horizontal cup drive gear 136 if a small amount of continuous paste flow is desired, or a gap could be allowed to exist between cup drive tube 138 and horizontal cup drive gear 136, so that some prophylaxis paste 130 could flow through paste entry hole 406 irrespective of its position with respect to horizontal cup drive gear 136. A preferred embodiment of the present invention may or may not be configured so that paste is expelled without pressure being applied to the cup.

In some situations, it may be preferred to have a dispensing notification system included in the prophy angle. A flexible noise-making member 474 could be coupled to the interior of prophy angle, so that it engages cup drive tube external gear engaging ridges 140 when cup drive tube 138 is depressed into prophy angle. An aural and tactile (vibration) notification can be provided to indicate that the paste is being dispensed.

Now referring to FIG. 5, there is shown a top view of horizontal cup drive gear 136, which shows it as having both internal and external teeth. More specifically, top side 410 of cup drive tube 138 is shown disposed in the toothed void in the center of horizontal cup drive gear 136.

In operation, the apparatus and method of the present invention as described in FIGS. 1–5, could function as follows:

The prophy angle 100 of the present invention is provided with prophylaxis paste 130 therein and is coupled to an external rotary power source. The power source is activated, causing the drive shaft 110 to rotate. This rotary motion causes drive shaft to disk initial couplings 124 to break, thereby allowing paste pressurizing spring 118 to move pressurizing plunger disk 114 along drive shaft 110, and thereby pressurizing the prophylaxis paste 130 in the prophy angle paste pressurization section 104 and the prophy angle head section 106 of the prophy angle 100. The rotary motion of drive shaft 110 also causes its drive shaft terminal vertical gear 112 to engage horizontal cup drive gear 136, which through cup drive tube external gear engaging ridges 140 causes cup drive tube 138 to turn prophy cup 108.

It should be noted that while the present invention is described as having a prophy cup which is driven with a rotary motion, it is intended to cover prophy cups which oscillate, reciprocate, vibrate or otherwise are driven in a non-rotary fashion. Non-rotary prophy cups have recently been introduced in the marketplace and are well known in the art.

Prophylaxis paste 130 flows through prophylaxis paste passageways 132. When pressure is applied along the longitudinal axis of cup drive tube 138, by pressing the prophy cup 108 to a patient's tooth, cup drive tube 138 is caused to translate through a central hole in horizontal cup drive gear 136. This upward translational motion is resisted by pressure sensitive valve spring 134, which will return cup drive tube 138 to its original position when such pressure is discontinued. When the pressure is applied, paste entry hole 406 moves from a "closed" configuration, where little or no paste flows therethrough, to an "open" position, where prophylaxis paste 130 is allowed to flow. The dotted line in FIG. 4 represents an "open" configuration of pressure sensitive valve 412. Paste entry hole in open position 406 is shown clearly above horizontal cup drive gear 136. Similarly, top side in open position 410 is shown above horizontal cup drive gear 136. The dentist is thereby able to control the flow rate by applying pressure to prophy cup 108. The flow rate is dependent upon the amount of pressure applied. If little or no pressure is applied, the present invention might be adapted to provide no prophylaxis paste 130 delivery. As pressure on the prophy cup 108 increases, paste entry hole 406 moves further into an open position. At first, a relatively low pressure will result in a slow flow rate. This flow rate will increase with pressure until a maximum flow rate is achieved when paste entry hole 406 is completely unobstructed.

The variable flow rate is not a necessary feature of all embodiments of the present invention. An "on" and "off" only design may be preferred by some practitioners.

Figure 6:
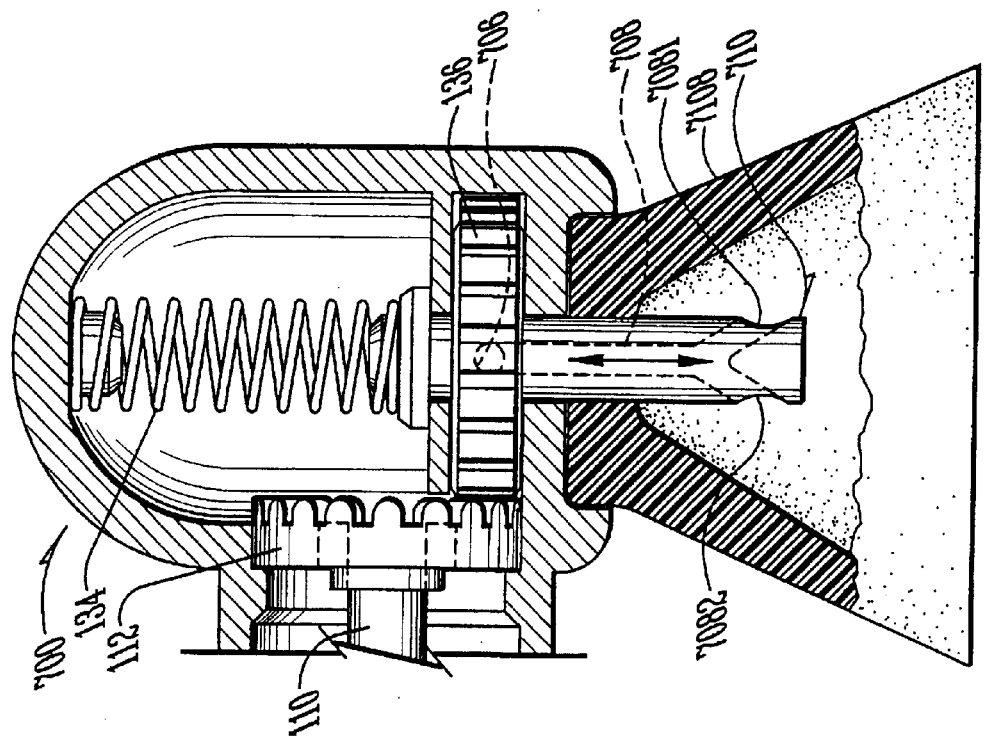
FIG. 6 is a cut-away side view of a head portion of an alternate embodiment of the present invention, where the dashed lines refer to concealed structural details.

Now referring to FIG. 6, there is shown an alternate embodiment of the present invention, generally designated 600, having a horizontal cup drive gear toothed region 636 of horizontal cup drive gear main body region 637, which engages with drive shaft terminal vertical gear 112. Horizontal cup drive gear main body region 637 is preferably designed, in combination with the prophy angle head exterior 639, to prohibit unwanted flow of prophylaxis paste to the outside of prophy cup 6108. The embodiment of this FIG. 6 is designed to permit a pausing of the rotation of the prophy cup 6108, during the time when prophylaxis paste or medium is being dispensed. This is accomplished when pressure is applied on the prophy cup 6108 and the cup drive tube 638 is translated inward with respect to horizontal cup drive gear main body region 637 and thereby exposing paste entry hole 606 and disengaging the rotation of the prophy cup 6108. The disengagement occurs when cup drive tube clutch plate 640 moves inward and first clutch tooth 642 and second clutch tooth 644 become disengaged with first clutch tooth engagement area 648 and second clutch tooth engagement area 646, respectively. Horizontal cup drive gear toothed region 636 continues to rotate, but cup drive tube clutch plate 640 and cup drive tube 638, which is attached thereto or integral therewith, becomes disengaged and stops rotating. When cup drive tube clutch plate 640 is disengaged and paste flows into paste entry hole 606, it then travels through paste delivery channel 608 to be dispensed into prophy cup 6108.

In some situations, it may be desirable to have some engagement or disengagement notification system, such as shown in clutch engagement rotary notification assembly 670. This arrangement includes a fixed noise-making member 672, which also can function as a stop to hold horizontal cup drive gear toothed region 636 in place. A disengageable rotating noise-making member 674 is coupled to the cup drive tube clutch plate 640. During normal operation (during times when not dispensing paste), fixed noise-making member 672 and disengageable rotating noise-making member 674 are constantly engaging each other as the cup drive tube clutch plate 640 rotates. When this noise stops, it is an indication that the dispensing process is under way. Depending upon the preference of the practitioner, alternate noise-making arrangements could be employed where the noise is only made during the dispensing process. Another possible notification system is shown which includes a switch actuating member 690 and a switch 694, which together cooperate and activate a disengagement notification lamp 680 when the cup drive tube clutch plate 640 is disengaged. The lamp 680 can be an LED or any other type of device capable of emitting light. Numerous other notification systems could be used as well.

The cup drive tube 638 is similar to cup drive tube 138 of FIGS. 1 and 4 except that it has a knurled tip 650, which is inserted into an undersized hole in prophy cup 6108. It may be desirable to include a slip-retarding collar 660 after the prophy cup 6108 has been positioned.

Figure 7:
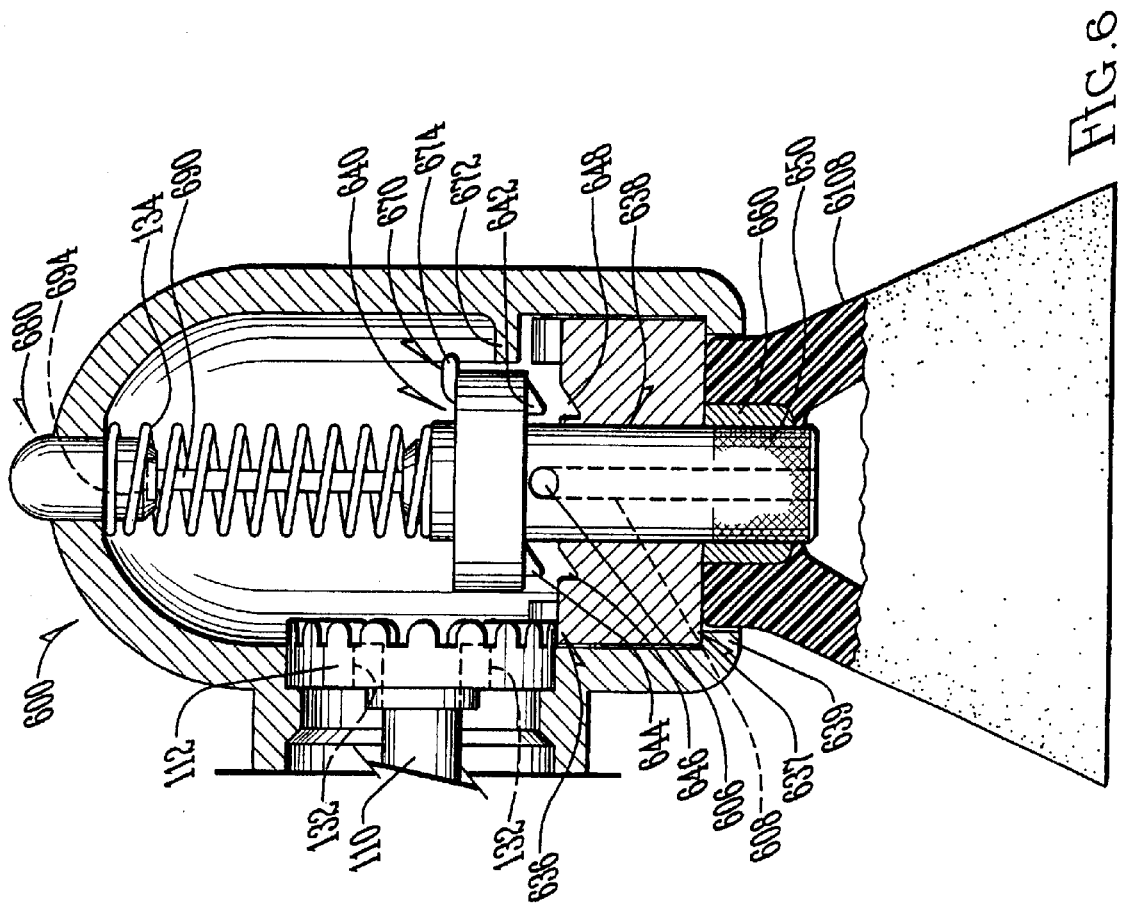
FIG. 7 is a view of an alternate embodiment of the present invention where the prophy cup does not translate to dispense the paste.

Now referring to FIG. 7, there is shown an alternate embodiment of the present invention generally designated 700, which is shown in a "normal" or "non-dispensing" configuration. Prophy angle 700 is different from those shown in FIGS. 1, 4, and 6, in that it is designed such that the prophy cup does not need to be moved in and out of the prophy angle 700 to result in dispensing the paste. Instead, a centrally disposed push button 710 receives pressure from engagement with a tooth and thereby causes paste entry hole 706 to move in a manner similar to paste entry hole 406, and paste entry hole 606 of FIGS. 4 and 6 respectively. Paste delivery channel 708 is shown having paste exit holes 7081 and 7082. Preferably push button 710 is a rubber or similar material which is sufficiently rigid to transmit pressure while not causing harm to the tooth with which it is engaging.

Figure 8:
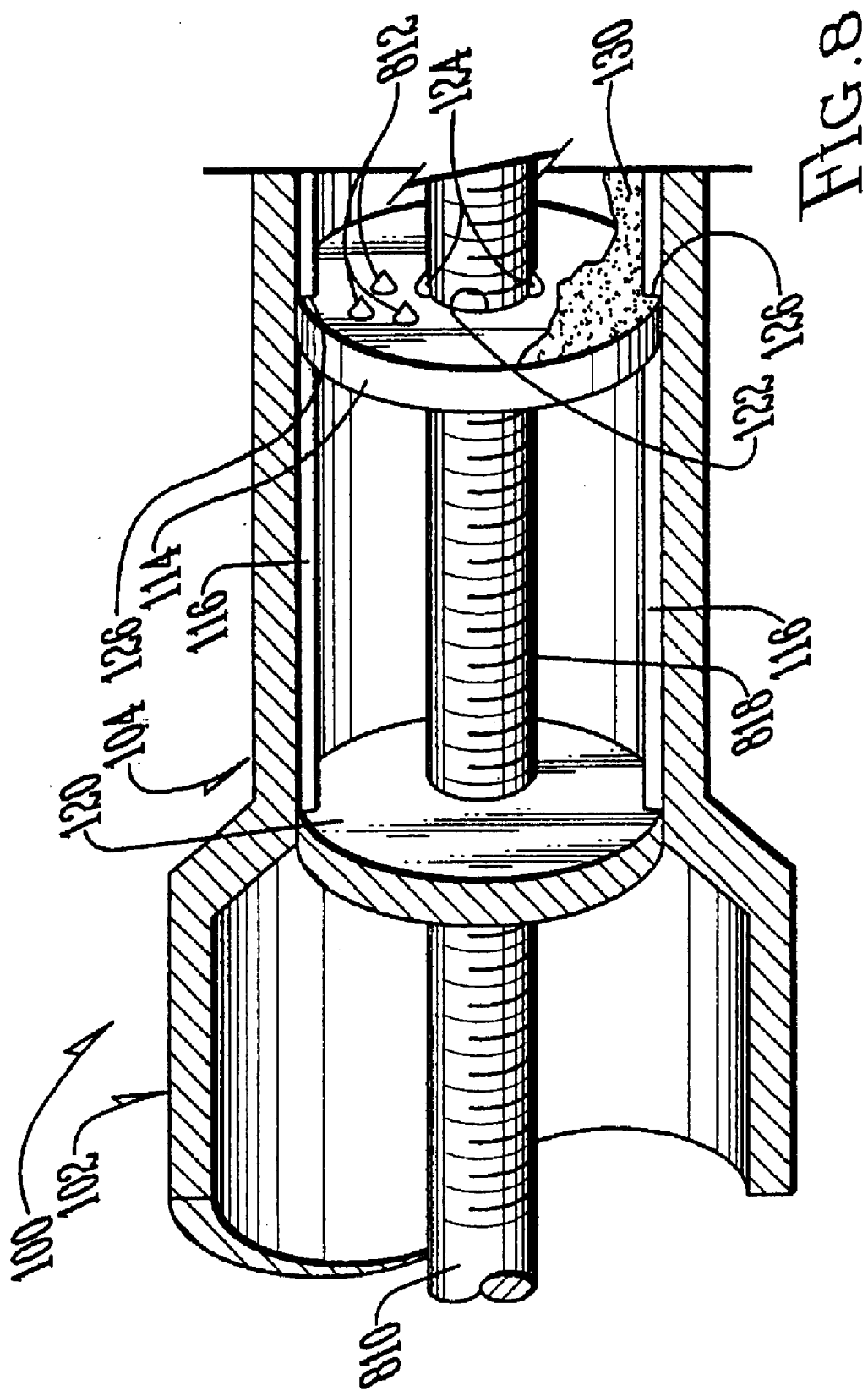
FIG. 8 is a cut-away side view of an alternate embodiment of the present invention having a different mechanism for maintaining pressure on the prophylaxis paste by advancing a plunger.

Now referring to FIG. 8, there is shown an alternate embodiment of the present invention which has an alternate mechanism for maintaining pressure on the prophylaxis paste by advancing a plunger. The spring 118 of FIG. 1 has been omitted and in its place is a threaded shaft 810 with threads 818 thereon. Pressurizing plunger disk 114 is caused to move along the threaded shaft 810 as pressurizing plunger disk 114 cooperates with the threads 818. Alignment ridges 116 can be used to prevent the pressurizing plunger disk 114 from spinning. When pressurizing plunger disk 114 is constrained from spinning, it is forced by the threads 818 to move along the threaded shaft 810. In another embodiment, the alignment ridges 116 may be omitted and frictional forces between the prophylaxis paste 130 and the pressurizing plunger disk 114 may provide the necessary resistance to spinning the pressurizing plunger disk 114. Paste engaging protuberances 812 may be added to increase the frictional forces between the disk 114 and the prophylaxis paste 130. Other structure or devices may be included as well. The paste engaging protuberances can be sized, shaped and configured to perform as a "high speed disengaging slip clutch." For example, when the rotation rate of the threaded shaft 810 reaches an upper threshold, the rotational forces applied by the pressurizing plunger disk 114 will exceed the frictional forces between the disk 114 and the paste 130. When this occurs, the disk will slip against the paste and permit at least some spinning of the disk, thereby reducing the speed at which the disk advances along the threaded shaft 810. The present invention can function as a "high pressure disengaging slip clutch." At low rotational speed of the threaded shaft and the prophy cup, some of the rotational force applied between the threaded shaft 810 and the disk 114 is used to advance the disk 114. If the pressure sensitive valve is made to restrict flow of paste, the pressure on the paste will eventually reach a point that the paste will not compress; i.e., the disk cannot advance. In such situations, the entire rotation forces are applied to the disk 114 and paste 130 interface where the frictional forces are overcome and the disk 114 begins to spin. This helps to provide a paste pressure which remains within a predetermined range of pressures. The inventor is now aware that other types of slip clutches could be employed as well.

In a pair of alternate embodiments of the present invention, one of the alignment ridges could be omitted, and the other could be deployed from a normal non-engaging position to a position of engagement in response to forces applied on the prophy angle by the operator. In the first example, the bottom alignment ridge 116 would be omitted, and the top alignment ridge would be retracted and configured to cooperate with the groove 126 only when an external button or bar (not shown) when pressed by the operator causes the top ridge 116 to descend and engage the groove 126. In an alternate embodiment, the top ridge is omitted, and the bottom ridge is configured to be recessed and not engaging the groove 126 unless it is acted upon by a similar button or bar along the bottom edge of the prophy angle. In yet a further embodiment, the retracting bottom ridge would be coupled with the second gear 136 or the cup drive tube 138. In such configurations, pressure applied on the prophy head 108 could be made to cause the bottom ridge 116 to engage the groove 126. In all of the specific embodiments with the movable ridges described in this paragraph, the disk 114 and the threaded shaft 810 would be configured so that the disk 114 will advance along the shaft 810 when one of the movable ridges engages one of the grooves 126.

Throughout this description, reference is made to prophy angles and prophylaxis paste because it is believed that the beneficial aspects of the present invention would be most readily apparent when used in connection with such matter; however, it should be understood that the present invention is not intended to be limited to such matter and should be hereby construed to include any liquids or gels instead of prophylaxis paste and be used in other non-professional cleaning situations as well. For example, prophy cup 108 could be a bristle brush and prophylaxis paste 130 could be toothpaste, liquid or gel. In such situations, the present invention could be a consumer toothbrush with automatic toothpaste delivery.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. An apparatus comprising:
   a prophy angle having a prophy cup attached thereto;
   a supply of matter disposed internal to said prophy angle; and,
   a pressure sensitive valve cooperating with said prophy cup, where said pressure sensitive valve is configured to control a flow of said matter to said prophy cup in a manner that is responsive to a pressure applied at least in part via said prophy angle.

2. An apparatus of claim 1 wherein said supply of matter is configured to deliver matter, under pressure, to said pressure sensitive valve.

3. An apparatus of claim 1 wherein said pressure sensitive valve is an analog valve and is responsive to pressure applied to a central pushbutton disposed in said prophy cup.

4. An apparatus of claim 1 wherein said pressure sensitive valve is configured to provide continuously variable flow rates of said matter as a function of variable mechanical pressure, within a predetermined range of mechanical pressures.

5. An apparatus of claim 4 wherein said pressure sensitive valve is configured to provide continuous variable flow rates which increase as mechanical pressure is increased by said prophy angle.

6. An apparatus of claim 5 wherein said supply of matter is configured to deliver matter to said pressure sensitive valve while under a fluid pressure.

7. An apparatus of claim 6 where said matter is a prophylaxis medium.

8. An apparatus of claim 7 wherein:
   said prophy angle includes a prophy angle paste pressurization section;
   said prophylaxis medium is a first color which is a darker color than a second color;
   wherein said second color is a color of said prophy angle paste pressurization section;
   said prophy angle paste pressurization section has a translucency characteristic which is configured to permit an external visual inspection of said prophy angle paste pressurization section to reveal prophylaxis medium disposed within said prophy angle paste pressurization section.

9. An apparatus of claim 8 wherein said pressure sensitive valve comprises:
   a cup drive tube coupled to said prophy cup, wherein said cup drive tube has a paste entry hole therein which is configured to receive said prophylaxis paste; and,
   means for biasing a valve, coupled to said cup drive tube, which is configured to bias said cup drive tube such that said paste entry hole is obstructed by an obstruction when no pressure is applied along a longitudinal axis of said cup drive tube.

10. An apparatus of claim 9 wherein said obstruction is a first gear which is coupled to said cup drive tube so that a rotation of said first gear results in a rotation of said cup drive tube.

11. An apparatus of claim 10 further comprising a drive shaft extending through said prophy angle paste pressurization section and having coupled at a first end a drive shaft terminal second gear, which is configured to cooperate with said first gear, said first gear and said second gear having an orthogonal relationship.

12. An apparatus of claim 11 where said supply of matter further includes a biased pressurizing plunger disk having a drive shaft orifice therethrough.

13. An apparatus of claim 12 wherein said biased pressurizing plunger is mated with said drive shaft via threads disposed on said drive shaft, said biased pressurizing plunger being biased in response to rotation of said drive shaft.

14. An apparatus of claim 13 wherein said biased pressurizing plunger is configured to resist rotation about a longitudinal axis of said drive shaft.

15. An apparatus for cleaning teeth comprising:
   means for transmitting power from a power source moving about a first axis to a second axis;
   wherein said means for transmitting is sized and configured to be inserted in a human mouth;
   means for removing matter disposed on a tooth;
   said means for removing is sized and configured to be inserted in a human mouth;
   means for regulating a flow rate of matter onto said means for removing, where said flow rate is responsive to pressure being applied to said means for removing;
   said means for regulating is sized and configured to be inserted in a human mouth;
   said means for regulating further being configured to permit adjustment of said flow rate while said means for regulating is at least partially disposed within a human mouth; and,
   said means for regulating further being configured to increase said flow rate as pressure applied to said means for removing increases.

16. An apparatus of claim 15 wherein said means for removing is a prophy cup and said first axis and said second axis are substantially orthogonal.

17. A method of adjusting a flow rate of matter into a prophy cup comprising the steps of:
   providing a prophy angle and a prophy cup in a human mouth-sized cavity;
   without removing said prophy angle from said cavity, increasing a level of pressure on said prophy cup, by applying pressure to said prophy angle and simultaneously contacting said prophy cup with a rigid object fixed in said cavity; and,
   without removing said prophy angle from said cavity and without inserting additional objects into said cavity which cooperate with and regulate said prophy angle, dispensing matter into said prophy cup at an increased flow rate when said level of pressure increases.

18. A method of claim 17 wherein:
   said step of dispensing matter includes the step of actuating a pressure sensitive valve coupled to said prophy cup by causing a hole in a tube to have increased direct exposure to a pressurized reservoir of a prophylaxis medium.

19. A prophylaxis material dispensing apparatus comprising:
   a first tooth engaging member, sized and configured to be inserted into a human mouth-sized cavity;
   an elongated member, coupled with said first engaging member, said elongated member configured to transmit mechanical force to said first tooth engaging member;
   said first tooth engaging member further configured to be powered into relative repeated motion with respect to said elongated member while said first tooth engaging member is disposed in said human mouth-sized cavity;
   a pressure sensitive prophylaxis material delivery control, coupled to said first tooth engaging member;

a prophylaxis material supply coupled to said pressure sensitive prophylaxis material delivery control for providing prophylaxis material to said pressure sensitive prophylaxis material delivery control; and, said pressure sensitive prophylaxis material delivery control being further configured to cause a variable flow rate of prophylaxis material to be responsive to mechanical pressure applied onto said first tooth engaging member.

20. An apparatus of claim 19 wherein said repeated motion is an oscillatory motion.

21. An apparatus of claim 19 wherein said repeated motion is a rotary motion.

22. An apparatus of claim 19 wherein said prophylaxis material supply further comprises a rotating threaded shaft and a movable end wall of a prophylaxis material reservoir, where a location of said movable end wall is responsive to said rotating threaded shaft.

23. An apparatus of claim 22 wherein said movable end wall is configured to move axially with respect to a longitudinal axis of said threaded shaft by cooperating with threads on said threaded shaft.

24. An apparatus of claim 23 wherein said movable end wall is configured to substantially move axially only when a movable ridge is caused to move from a non-engaging position to an engaging position with respect to a groove in said movable end wall.

25. An apparatus of claim 24 wherein said movable ridge is responsive to a force applied thereon by said pressure sensitive prophylaxis material delivery control.

26. An apparatus of claim 24 wherein said movable ridge is responsive to an external button on said elongated member.

* * * * *